(12) United States Patent
Py (10) Patent No.: US 7,168,746 B2
(45) Date of Patent: *Jan. 30, 2007

(54) APPARATUS FOR APPLYING AND REMOVING CONTACT LENSES AND RELATED METHOD

(75) Inventor: Daniel Py, Larchmont, NY (US)

(73) Assignee: Medical Instill Technologies, Inc., New Milford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/137,866

(22) Filed: May 23, 2005

(65) Prior Publication Data

US 2006/0017297 A1    Jan. 26, 2006

Related U.S. Application Data

(60) Provisional application No. 60/573,996, filed on May 24, 2004, provisional application No. 60/520,609, filed on Nov. 17, 2003, provisional application No. 60/288,030, filed on May 2, 2001.

(51) Int. Cl.
  *A61F 9/00* (2006.01)
(52) U.S. Cl. ..................................... 294/1.2
(58) Field of Classification Search ............. 294/1.2, 294/64.1; 606/107; 206/5.1
  See application file for complete search history.

(56) References Cited

U.S. PATENT DOCUMENTS

| 2,919,696 | A | 1/1960 | Rinaldy |
| 3,091,328 | A | 5/1963 | Leonardos |
| 3,139,298 | A | 6/1964 | Grabiel |
| 3,304,113 | A | 2/1967 | Hutchison |
| 3,600,028 | A | 8/1971 | Henning |
| 3,879,076 | A | 4/1975 | Barnett |
| 3,910,618 | A | 10/1975 | Massenz |
| 4,037,866 | A | 7/1977 | Price |
| 4,071,272 | A | 1/1978 | Drdlik |
| 4,079,976 | A | 3/1978 | Rainin et al. |
| 4,093,291 | A | 6/1978 | Schurgin |
| 4,113,297 | A | 9/1978 | Quinn |
| 4,200,320 | A | 4/1980 | Durham |
| 4,201,408 | A | 5/1980 | Tressel |
| 4,240,465 | A | 12/1980 | Rader |
| 4,244,466 | A | 1/1981 | Arnhem |

(Continued)

FOREIGN PATENT DOCUMENTS

DE    2434319 B1    1/1976

(Continued)

*Primary Examiner*—Dean J. Kramer
(74) *Attorney, Agent, or Firm*—McCarter & English, LLP (57) ABSTRACT

An apparatus and method are provided for applying and removing contact lenses. The apparatus has an actuator and two tissue-engaging surfaces drivingly coupled to the actuator for engaging tissue adjacent to the eye in connection with actuating the actuator and to facilitate retaining the eye open during removal of the contact lens therefrom. A support surface supports the apparatus adjacent to the eye, and a lens removing member is drivingly coupled to the actuator for movement between an extended position and a retracted position for removing the contact lens from the eye. The actuator actuates the tissue-engaging surface to facilitate retaining the eye open during removal of the contact lens therefrom, and substantially simultaneously actuates the lens removing member to remove the contact lens from the open eye.

27 Claims, 5 Drawing Sheets

U.S. PATENT DOCUMENTS

| | | |
|---|---|---|
| 4,308,947 A | 1/1982 | Arnhem |
| 4,378,126 A | 3/1983 | Procenko |
| 4,387,921 A | 6/1983 | Licata |
| 4,565,396 A | 1/1986 | Larimer |
| D286,137 S | 10/1986 | Huck et al. |
| 4,784,652 A | 11/1988 | Wikstrom |
| 4,792,334 A | 12/1988 | Py |
| 4,908,024 A | 3/1990 | Py |
| 4,946,452 A | 8/1990 | Py |
| 4,981,479 A | 1/1991 | Py |
| 5,069,494 A | 12/1991 | Reinson et al. |
| 5,085,651 A | 2/1992 | Py |
| 5,133,702 A | 7/1992 | Py |
| 5,163,929 A | 11/1992 | Py |
| 5,246,259 A | 9/1993 | Hellenkamp et al. |
| 5,267,986 A | 12/1993 | Py |
| 5,300,115 A | 4/1994 | Py |
| 5,320,845 A | 6/1994 | Py |
| 5,353,956 A | 10/1994 | Wilson |
| 5,366,499 A | 11/1994 | Py |
| 5,401,259 A | 3/1995 | Py |
| 5,407,241 A | 4/1995 | Harrison |
| D362,462 S | 9/1995 | Carlson et al. |
| RE35,187 E | 3/1996 | Gortz |
| D368,774 S | 4/1996 | Py |
| 5,538,301 A | 7/1996 | Yavitz et al. |
| 5,558,374 A | 9/1996 | Harrison |
| D374,719 S | 10/1996 | Py |
| 5,613,957 A | 3/1997 | Py |
| 5,649,727 A | 7/1997 | St. Louis |
| 5,685,869 A | 11/1997 | Py |
| 5,688,007 A | 11/1997 | Jefferson |
| 5,695,049 A | 12/1997 | Bauman |
| 5,732,990 A | 3/1998 | Yavitz et al. |
| 5,785,370 A | 7/1998 | Pomerantz |
| 5,875,931 A | 3/1999 | Py |
| 5,913,556 A | 6/1999 | Perusse |
| 5,941,583 A | 8/1999 | Raimondi |
| 5,944,702 A | 8/1999 | Py |
| RE36,410 E | 11/1999 | Meshberg |
| 6,033,384 A | 3/2000 | Py |
| RE37,047 E | 2/2001 | Py |
| 6,213,982 B1 | 4/2001 | Py |
| 6,302,101 B1 | 10/2001 | Py |
| 6,398,277 B1 | 6/2002 | McDonald |
| 6,401,915 B1 | 6/2002 | Faxe |
| 6,471,052 B2 | 10/2002 | Faxe et al. |
| D466,008 S | 11/2002 | Michaels |
| D468,105 S | 1/2003 | Beach |
| 6,572,165 B2 | 6/2003 | Faxe et al. |
| 6,739,636 B2 | 5/2004 | Py |
| D491,461 S | 6/2004 | Grant |
| 7,000,960 B2 * | 2/2006 | Py .......................... 294/1.2 |
| 2002/0017294 A1 | 2/2002 | Py |
| 2002/0074362 A1 | 6/2002 | Py |

FOREIGN PATENT DOCUMENTS

| | | |
|---|---|---|
| DE | 3822654 A1 | 1/1990 |
| DE | 3920919 A1 | 1/1990 |
| FR | 1401116 | 7/1964 |
| FR | 2481472 | 10/1981 |
| FR | 2496906 | 6/1982 |
| FR | 2525472 | 10/1983 |
| GB | 2001778 A | 2/1979 |
| JP | 61018920 | 1/1986 |
| JP | 02023960 | 1/1990 |
| WO | WO 81/02287 | 8/1981 |
| WO | WO 93/04648 | 3/1993 |
| WO | WO 01/10367 | 2/2001 |

* cited by examiner

APPARATUS FOR APPLYING AND REMOVING CONTACT LENSES AND RELATED METHOD

CROSS-REFERENCE TO RELATED APPLICATIONS

This application claims priority to U.S. Provisional Application Ser. No. 60/573,996, filed May 24, 2004, titled "Apparatus for Applying and removing Contact Lenses and Related Method", which is hereby incorporated by reference in its entirety. This patent application also discloses subject matter similar to that disclosed in U.S. application Ser. No. 10/139,192, filed May 2, 2002, entitled "Contact Lens Applicator and Cartridge Used in Connection Therewith", now U.S. Pat. No. 6,739,636, which claims priority to U.S. Provisional Patent Application No. 60/288,030, filed May 2, 2001, and to co-pending U.S. Provisional Application No. 60/520,609, filed Nov. 17, 2003, entitled "Contact Lens Transfer Device And Associated Method", each of which is assigned to the Assignee of the present invention and also is hereby expressly incorporated by reference as part of the present disclosure.

FIELD OF THE INVENTION

The present invention relates to ocular apparatus, and more particularly, to such apparatus for removing and applying contact lenses to an eye.

BACKGROUND INFORMATION

Many patients who require optical correction for visual acuity wear eye-glasses because they either cannot, or do not desire to apply contact lenses to their eyes. Among those who are able to apply contact lenses to their eyes without assistance, it is believed that approximately 25% of these patients have terminated use of contact lenses because of complications arising from a lack of aseptic conditions and/or because of frustrations or difficulties arising from the need to clean and store the contact lenses, and transport with themselves the necessary containers and cleaning solutions to maintain the contact lenses. For example, the containers for holding contact lenses need to be carefully cleaned and are difficult, and in many cases, impossible to adequately clean. In addition, these persons typically require a mirror to apply the contact lenses, and because they have difficulty viewing themselves within the mirror without eyeglasses, they have further difficulty applying the contact lenses to their eyes without assistance.

Many ocular complications relating to contact lenses are due to infections and/or toxic reactions arising from incomplete rinsing of the contact lenses with cleaning solutions or otherwise inadequate cleaning or not maintaining the sterile conditions of the lenses prior to application to the eyes. A certain number of such complications are due to the preservatives contained within the cleaning solutions. For example, it has been widely demonstrated that certain preservatives are aggressive, irritating and/or damaging to the superficial layers of the cornea of the eye.

There are numerous events that must be carried out to properly apply contact lenses to a person's eyes, including: forcing the upper and lower eyelids in a wide-open position so that the contact lens (typically about 14.5 mm in outer diameter) can fit through the opening between the eyelids; adequately cleaning the finger(s) used to handle and apply the contact lens; making sure the contact lens is properly oriented with the correct side (or concave side) facing the eye; making sure the contact lens is in a state of equilibrium on the finger at the time of application; and applying the contact lens onto the cornea of the eye without irritating the cornea or otherwise causing the eye to blink during application. The sensitivity of the cornea is among the highest of the human tissues, and therefore if the eyelids are not maintained in the proper position during application of the contact lens, the maneuver fails. Similarly, contact lens removal requires forcing the upper and lower eyelids in the wide-open position so that the finger tips and contact lens can fit through the opening between the eyelids; adequately cleaning the finger(s) used to pinch or otherwise handle and remove the contact lens from the eye; and removing the contact lens from the cornea of the eye without pushing the contact lens underneath one of the eyelids, irritating the cornea or damaging the lens.

In view of the above, several attempts have been made to aid a person when applying a contact lens. For example, U.S. Pat. No. 2,919,696 to Rinaldy shows an instrument for applying a contact lens. The instrument has a cup member 11 with a rim 13. A bracket 14 supports a lens supporting element 20 which is slidably mounted within the cup member 11. In use, the lens supporting element 20 is retracted and retains the lens by surface tension. The rim 13 is manually deformed and placed against the eyelids so that upon relaxing the rim 13, the eyelids are retained open. Subsequently, the lens supporting element 20 is depressed to place the contact lens on the eye and the instrument is removed.

U.S. Pat. No. 3,910,618 to Massenz provides a contact lens applicator having a cup 11 connected to an irrigation bottle 23 by a tube 14. The tube 14 slides within the cup 11 and communicates fluid into the cup 11 from the irrigation bottle 23. The end of the tube within the cup 11 has a lens seat 19 for receiving a contact lens. The distal end of the cup 11 is a rim 12. Both the rim 12 and the cup are made of rubber. In operation, the rim 12 is squeezed to bring the outer edges together. The rim 12 is applied to the eyelid. Upon relief of the compression, the cup 11, being resilient, resumes shape keeping the eye widely exposed. Then, the tube 14 is moved toward the eye to place a contact lens thereon and the irrigation bottle 23 provides fluid as desired.

U.S. Pat. No. 4,113,297 to Quinn illustrates a device for inserting and removing a contact lens 32. A stand 11 supports the device upright on a flat surface. A storage chamber 15 is in fluid communication with a float chamber 14. An applicator eyepiece 16 mounts on top of the float chamber 14 and defines an aperture. A rod member 20 extends through the aperture and receives a contact lens on its top. The height of the rod member 20 is determined by the fluid level within the float chamber 14. Actuation of a flexible portion of the storage chamber 15 varies the fluid level within the float chamber 14 and, thus, the height of the rod member 20. To apply a contact lens, the fingers of one hand are used to hold the eye open over the eyepiece 16. The free hand actuates the storage chamber 15 to raise the rod member 20 to place the contact lens on the eye.

U.S. Pat. No. 5,069,494 to Reinson et al. shows a contact lens applicator 25 which also stores a plurality of contact lens. The container portion 10 includes multiple portions 10 which are identical and interlocking. Each portion 10 contains a single contact lens disposed in a liquid. The lens is supported on a deformable projection made of five legs 20. The portions 10 have a cover surface 16 and sidewalls with inner threads 13 and outer threads 14. The inner threads 13 and outer threads 14 of adjacent portions 10 threadably engage such that the adjacent portion 10 defines the cover for the next adjacent portion 10. A base 12 upon which the contact lens rests completes the portions 10.

There are problems associated with each of these prior art inventions such as contamination from fingers, a significant skill level being required to use the device, and no means to facilitate retaining the eyelids open simultaneously with insertion and/or removal of the lens. Accordingly, it is an object of the present invention to provide an apparatus and method that overcomes one or more of the drawbacks and/or disadvantages associated with prior art apparatus and methods for removing and/or handling contact lenses.

SUMMARY OF THE INVENTION

In accordance with one aspect, the present invention is directed to an apparatus comprising at least one actuator, and at least one tissue-engaging surface drivingly coupled to the actuator for engaging tissue adjacent to the eye in connection with actuating the actuator and to facilitate retaining the eye open during removal of the contact lens therefrom. A support surface supports the apparatus adjacent to the eye, and a lens removing member is drivingly coupled to the actuator for movement between an extended position and a retracted position for removing the contact lens from the eye. The actuator actuates the tissue-engaging surface to facilitate retaining the eye open during removal of the contact lens therefrom, and substantially simultaneously actuates the lens removing member to remove the contact lens from the open eye.

In one embodiment of the present invention, the lens removing member includes a contact lens support surface, at least one fluid-flow aperture extending through the lens support surface, and a suction chamber coupled in fluid communication with the fluid-flow aperture for drawing fluid through the fluid-flow aperture and, in turn, moving the lens from the eye and onto the lens support surface. In one such embodiment, the suction chamber is a variable-volume chamber movable between contracted and expanded positions for drawing fluid through the fluid-flow aperture and into the chamber. In one such embodiment, the variable-volume chamber is defined by a bellows.

In accordance with another aspect, the present invention is directed to a method for removing a contact lens from an eye, comprising the following steps:

(i) providing an apparatus including a lens removing member movably mounted thereon, at least one actuator for moving the lens removing member between an extended position and a retracted position, and at least one tissue-engaging surface drivingly coupled to the actuator and movably mounted on the apparatus;

(ii) placing the apparatus adjacent to the eye with the at least one tissue-engaging surface in contact with facial tissue adjacent to the eye; and (iii) actuating the actuator to move the at least one tissue-engaging surface against facial tissue adjacent to the eye and facilitate retaining the eye open, move the lens removing member from the retracted to the extended position and, in turn, transfer the lens from the eye onto the lens removing member.

In one embodiment of the present invention, the method further comprises the step of drawing fluid through the lens removing member to, in turn, draw the lens from the eye and onto the lens removing member. In accordance with one such embodiment, the fluid is drawn through the lens removing member in connection with moving the lens removing member from the retracted position to the extended position.

One advantage of the present invention is that the apparatus and method permit a contact lens to be removed from the eye without the user touching either the lens or the eye. Another advantage of a currently preferred embodiment of the present invention is that the apparatus may be configured for both applying contact lenses to the eyes and removing the contact lenses from the eyes.

Other objects and advantages of the present invention will be become more readily apparent in view of the following detailed description of the currently preferred embodiment and the accompanying drawings.

DETAILED DESCRIPTION OF THE CURRENTLY PREFERRED EMBODIMENT OF THE INVENTION

Referring to FIGS. 1 through 5, an apparatus embodying the present invention for applying and removing contact lenses is indicated generally by the reference numeral 10. The apparatus 10 comprises a housing assembly 12 including a hollow, elongated housing 14, an actuator or trigger 16 pivotally mounted by a pin 18 on one side of the housing 14 and defining a first finger grip 20, and a second finger grip 22 mounted on an opposite side of the housing 14. A roller 24 is rotatably mounted on one side of an open proximal end 26 of the housing 14, and a curved cantilever 28 is pivotally mounted on an opposite side of the open proximal end 26 relative to the roller 24. The roller 24 is drivingly coupled to the trigger 16 and defines a first peripheral tissue-engaging surface 30 for engaging tissue adjacent to the eye in connection with actuating the trigger to facilitate retaining the eye open during contact lens application and removal. Similarly, the curved cantilever 28 is drivingly coupled to the trigger 16 and defines a second tissue-engaging surface 32 for engaging tissue adjacent to the eye in connection with actuating the trigger to facilitate retaining the eye open during contact lens application and removal.

Figure 4:
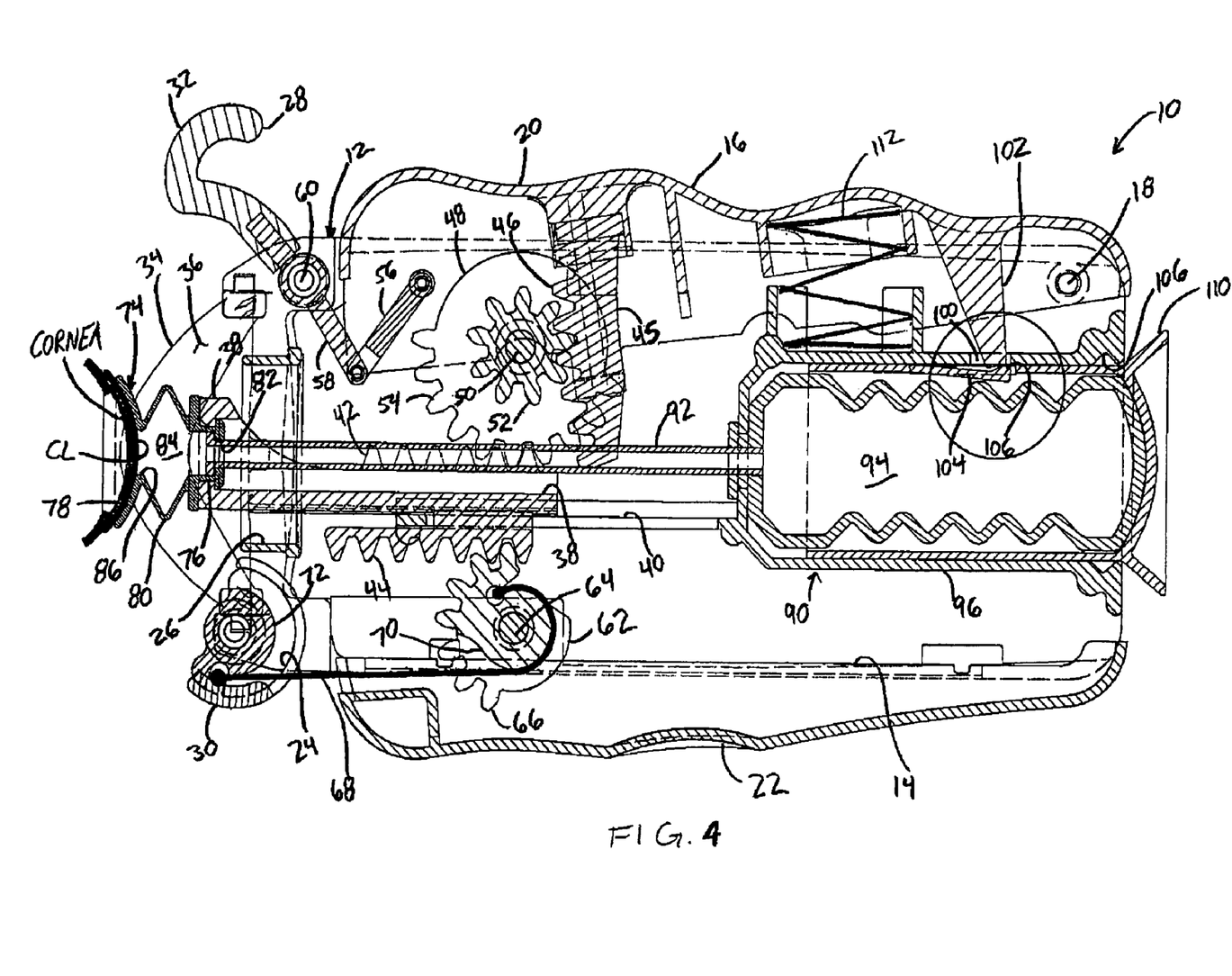
FIG. 4 is a cross-sectional view of the apparatus of FIG. 1 illustrating the trigger in an actuated position to move the tissue-engaging surfaces and facilitate retaining the eye open during contact lens removal, to move the lens holder and remover into contact with a contact lens on the eye, and to actuate the bellows to draw air or other fluid through the lens holder and remover and transfer the lens by suction thereon.
Figure 5:
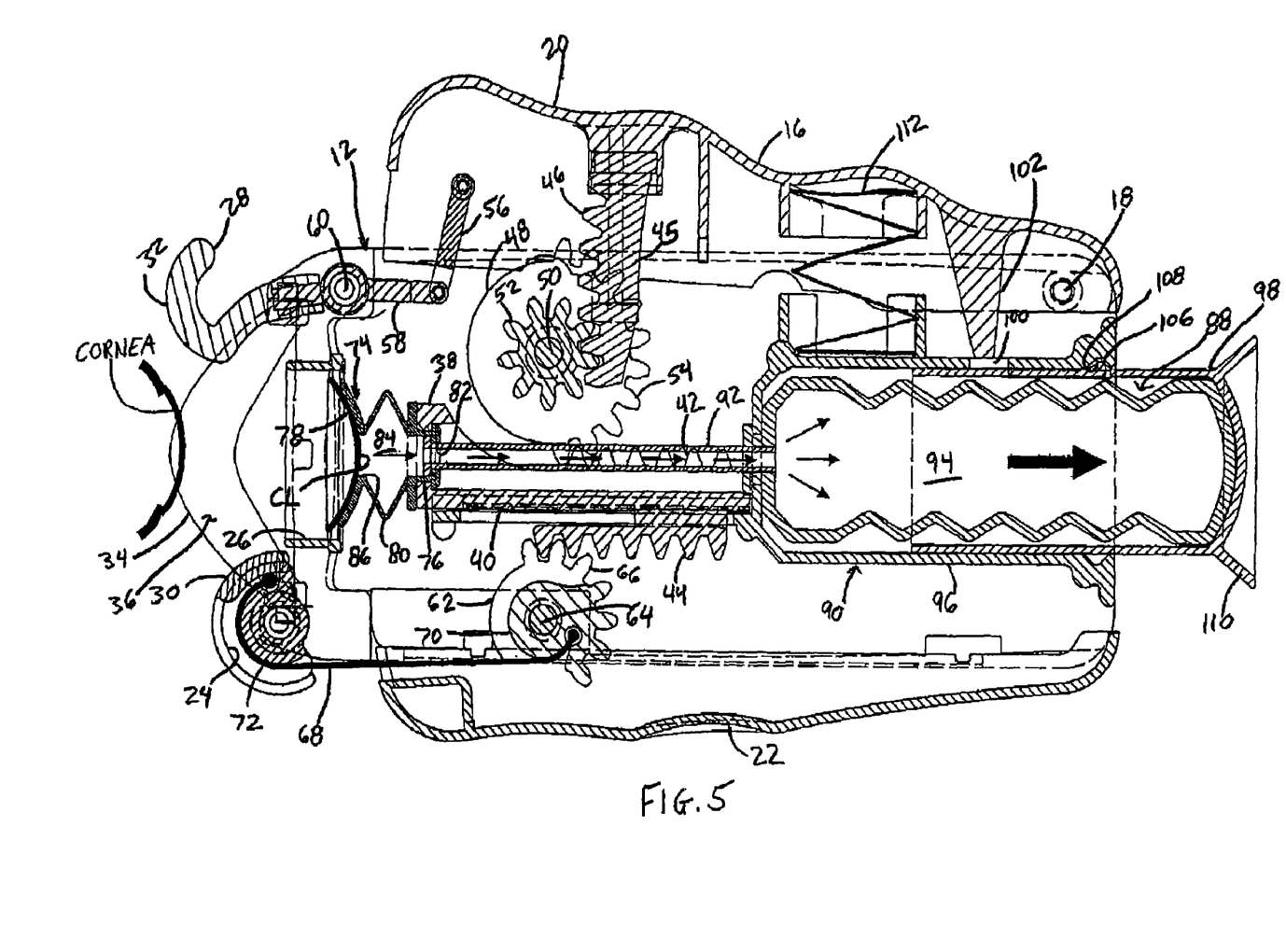
FIG. 5 is a cross-sectional view of the apparatus of FIG. 1 illustrating the contact lens removed from the eye, the lens holder and remover withdrawn into the interior of the housing, and the bellows in an extended position for drawing air or other fluid through the lens holder and remover to facilitate transfer of the lens from the eye thereon.

A pair of wing-shaped members 34 (only one shown) project outwardly from opposite sides of the tissue-engaging surfaces 30, 32 relative to each other, and each defines a support surface 36 for contacting the facial tissue surrounding a person's eye to, in turn, facilitate locating the apparatus 10 over the eye to either apply a contact lens "CL" to the eye (see FIG. 1), or to remove the contact lens CL from the eye (see FIGS. 4 and 5). The wing-shaped members 34 preferably define the shape of a typical eyecup for comfortably engaging the facial tissue surrounding the eye. Preferably, the wing-shaped members 34 are each pivotally mounted to the housing 14 so that they may be folded inwardly for storage and opened outwardly for use. As may be recognized by those skilled in the pertinent art based on the teachings herein, the wing-shaped members 34 may be incrementally adjustable to fix the wing-shaped members at any of a plurality of different positions to thereby accommodate user's having different facial dimensions. Alternatively, the wing-shaped members may not be movably mounted on the body, but rather the support surfaces may be defined by a fixed portion of the housing forming an eye cup.

The apparatus 10 further includes a drive member or pusher 38 slidably mounted on a slide 40 that is, in turn, fixedly mounted within the interior of the housing 14. The drive member 38 includes a first rack of gear teeth 42 on one side thereof, and a second rack of gear teeth 44 on an opposite side thereof The trigger 16 includes on an interior side thereof an actuating arm 45 including on a proximal side thereof a third rack of gear teeth 46. A first gear assembly 48 is rotatably mounted by a pin 50 on an interior wall of the housing 14, and includes an inner sprocket 52 that meshes with the third rack 46 of the actuating arm 45, and an outer sprocket 54 that meshes with the first rack 42 of the drive member 38. Manually depressing the trigger 16 inwardly causes the actuating arm 45 to rotatably drive the first gear assembly 48 in a clockwise direction which, in turn, causes the drive member 38 to move axially outwardly toward and partially through the open proximal end 26 of the housing 14.

A first linkage 56 is pivotally mounted on one end to a proximal end of the trigger 16, and is pivotally connected on its other end to a second linkage 58. The second linkage 58 is pivotally mounted by a pin 60 on the proximal end of the housing 14, and is fixedly secured on its side opposite the pin 60 to the curved cantilever 28. Manually depressing the trigger 16 inwardly causes the first linkage 56 to pivot the second linkage 58 which, in turn, causes the curved cantilever 28 to pivot in a generally clockwise arcuate direction. Accordingly, when the apparatus 10 is placed over a user's eye, the second tissue-engaging surface 32 of the curved cantilever engages the facial tissue above the eye, and cooperates with the first tissue-engaging surface 30 of the roller 24 to facilitate retaining the eye open during contact lens application and removal.

A second gear assembly 62 is rotatably mounted by a pin 64 on an interior wall of the housing 14 on an opposite side of the drive member 38 relative to the first gear assembly 48, and includes an outer sprocket 66 that meshes with the second rack 44 of the drive member 38. A drive cable 68 is fixedly secured on one end to the second gear assembly 62 and is positioned to be wrapped partially over a spool-like surface 70 of the second gear assembly. The drive cable 68 is fixedly secured at its other end to the roller 24 and is positioned to be wrapped partially over an interior spool-like surface 72 of the roller. As indicated above, manually depressing the trigger 16 inwardly causes the drive member 38 to move axially outwardly which, in turn, rotatably drives the second gear assembly 62 in a counterclockwise direction. This, in turn, causes the drive cable 68 to rotate the roller 24 in a counterclockwise direction. Accordingly, when the apparatus 10 is placed over a user's eye, the first tissue-engaging surface 30 of the roller 24 engages the facial tissue below the eye, and cooperates with the second tissue-engaging surface 32 of the curved cantilever 28 to facilitate in retaining the eye open during contact lens application and removal.

As may be recognized by those of ordinary skill in the pertinent art based on the teachings herein, the tissue-engaging surfaces 30, 32 may take any of numerous different shapes and/or configurations that are currently known, or that later become known for performing the functions of these components as disclosed herein. For example, the surfaces may be coated with a resilient polymeric material to facilitate comfortable engagement and movement of the facial tissue adjacent to the eye to facilitate retaining the eye open during contact lens application or removal. In addition, the first and second tissue-engaging surfaces 30, 32 may be defined by two curved cantilevers, two rollers, a combination of a curved cantilever and roller as shown, or other devices. The present inventor has determined that the illustrated combination wherein the lower tissue-engaging surface 30 is formed by a roller, and the upper tissue-engaging surface 32 is formed by the curved cantilever is particularly suited for contact lens application and removal. The lower roller tends to move the lower eyelid to a lesser extent than the upper eyelid and to hold the lower eyelid in place, whereas the upper cantilever tends to move the upper eyelid to a greater extent than does the roller with respect to the lower eyelid.

Figure 1:
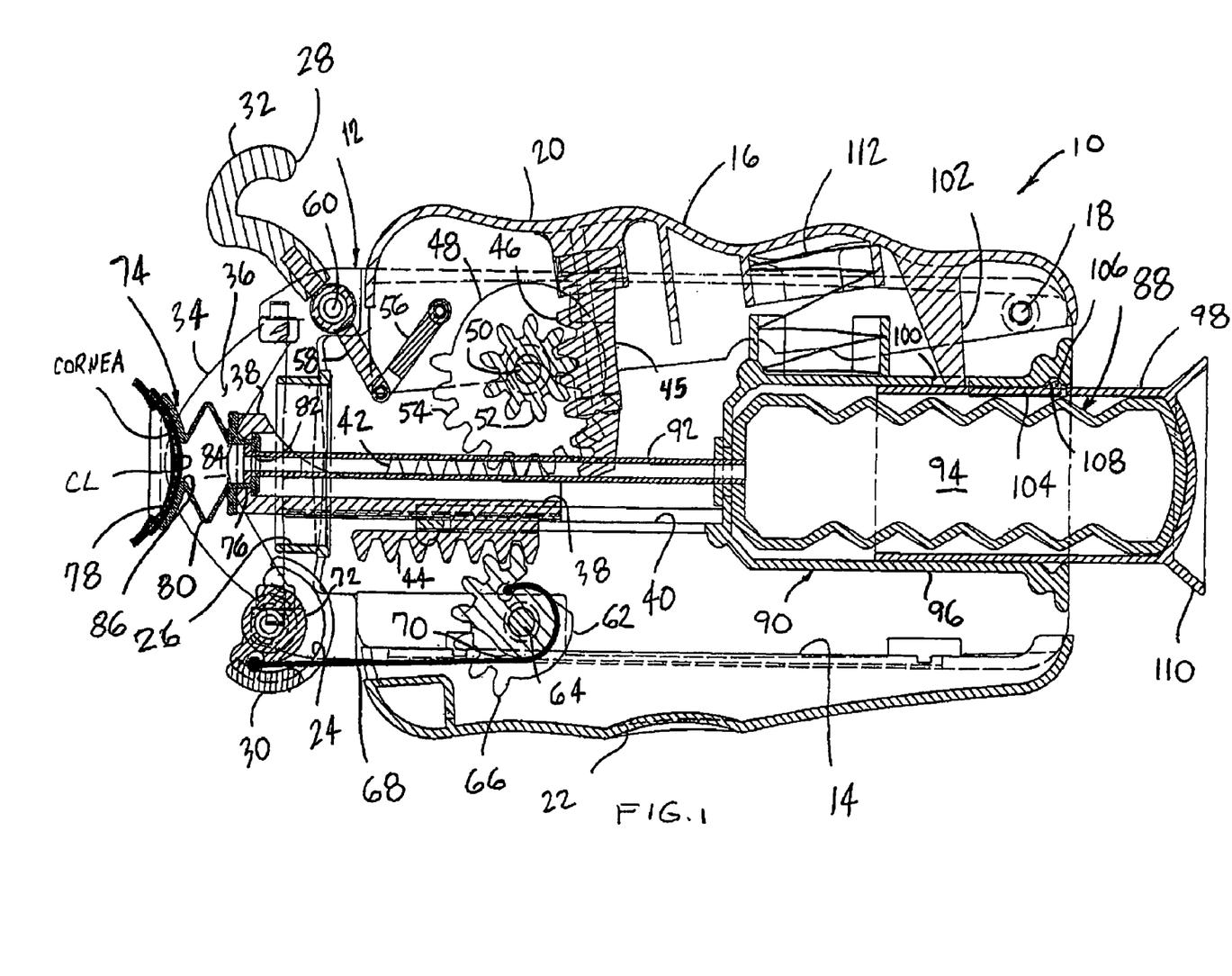
FIG. 1 is a cross-sectional view of an apparatus embodying the present invention for applying a contact lens to an eye and for removing the contact lens therefrom, and illustrating the trigger of the apparatus in an actuated position and the lens holder and remover of the apparatus in an extended position for applying a contact lens to an eye.
Figure 2:
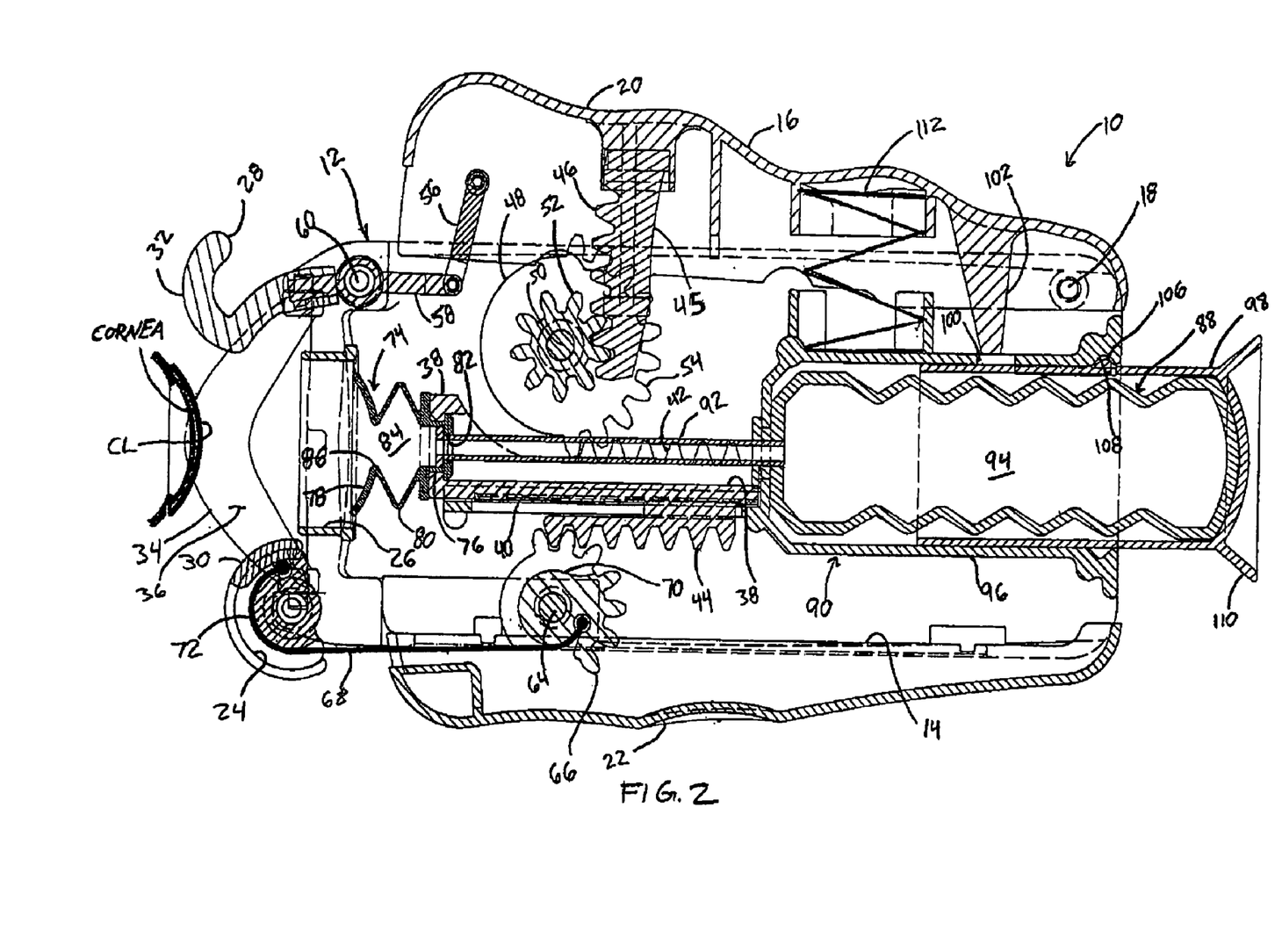
FIG. 2 is a cross-sectional view of the apparatus of FIG. 1 illustrating the trigger in its normal position with the lens holder and remover axially withdrawn into the interior of the housing and the bellows in an unloaded state.

The apparatus 10 further includes a contact lens holder and remover 74 mounted on the proximal end of the drive member 38 for both applying a contact lens CL to an eye, as shown typically in FIG. 1, and for removing a contact lens CL from an eye, as shown typically in FIGS. 4 and 5. The contact lens holder and remover 74 includes a base 76 connected to the proximal end of the drive member 38, a lens support surface 78 for supporting a contact lens CL thereon, and a bellows or like flexible portion 80 extending between the lens support surface 78 and base 76. The lens support surface 78 is made of a soft, elastomeric material. If desired, the lens support surface 78 made be made of a material that is softer than the contact lens CL itself. However, as may be recognized by those of ordinary skill in the pertinent art based on the teachings herein, the lens support surface (and/or the lens holder and remover) may be made of any of numerous different materials that are currently known, or that later become known for performing the function of the lens holder and remover as disclosed herein. In addition, the lens support surface 78 may include angularly spaced protuberances thereon, as described in the above-mentioned co-pending patent application, or may take any of numerous different shapes and/or configurations that are currently known, or that later become known for performing the function(s) of the lens holder and remover as disclosed herein.

The base 76 of the lens holder and remover 74 defines a peripheral groove that receives therein an annular protuberance formed on the proximal end of the drive member 38 to connect the lens holder and remover to the drive member. The base 76 of the lens holder and remover 74 further defines a fluid-flow aperture 82 extending through a bottom wall thereof that is in fluid communication with a fluid chamber 84 formed within the interior of the bellows 80, and the interior chamber 84 is, in turn, connected in fluid communication with a fluid-flow aperture 86 formed in a central portion of the lens support surface 78.

The apparatus 10 further includes a suction bellows 88 received within a bellows housing 90 mounted within a base portion of the housing 14. A flexible suction tube 92 is connected in fluid communication on one end to the fluid-flow aperture 82 of the lens holder and remover 74, and is connected in fluid communication on its other end to the bellows 88. Although not shown in the drawings for simplicity, when the lens holder and remover 74 is located in the normal or rest position shown typically in FIGS. 2, 3 and 5, the flexible suction tube 92 is either bent or forms one or more loops to accommodate the shorter axial distance between the lens holder and remover 74 and the suction bellows 88 in comparison to such axial distance when located in the actuated or extended positions shown typically in FIGS. 1 and 4. The bellows 88 defines an interior, variable-volume suction chamber 94, and is movable between a contracted position, shown typically in FIG. 4, wherein the variable-volume suction chamber 94 defines a first volume, and an extended position, shown typically in FIG. 5, wherein the variable-volume suction chamber 94 defines a second volume greater than the first volume. When the bellows 88 transitions from the contracted position of FIG. 4 to the extended position of FIG. 5, and as indicated by the arrows in FIG. 5, fluid is drawn through the fluid-flow aperture 86 in the lens support surface 76, through the bellows chamber 84 of the lens holder and remover 74, through the suction tube 92, and into the variable-volume suction chamber 94 of the bellows 88. As described further below, and shown typically in FIGS. 4 and 5, the suction or vacuum created by the fluid flowing inwardly through the fluid-flow aperture 86 in the lens holder and remover 74 is sufficient to transfer the contact lens CL from the eye onto the lens holder and remover 74 to thereby remove the contact lens CL from the eye.

The bellows housing 90 includes a female housing 96 formed within the base of the housing 14 and receives therein the bellows 88, and a male housing 98 slidably received within the female housing 96 with the bellows 88 seated therebetween. The female housing 96 defines on a side wall thereof facing the trigger 16 an actuation aperture 100, and the trigger 16 includes a bellows actuator 102 that extends laterally inwardly and is receivable through the actuation aperture 100 when the actuator or trigger is pivoted laterally inwardly. The male bellows housing 98 includes in a side wall thereof a flexible tang 104 defining a lobe 106 on an outer side thereof As shown typically in FIG. 3, when the bellows 88 is in the contracted position, the lobe 106 of the tang 104 is received within the actuation aperture 100 to retain the bellows in the contracted (or "loaded") position. As shown typically in FIGS. 4 and 5, when the trigger 16 is pivoted laterally inwardly, the second actuating arm 102 of the trigger engages and depresses laterally inwardly the lobe 106 of the tang 104 to thereby release the male housing 98 from the female housing 96. Then, the spring force of the contracted bellows 88 drives the bellows axially outwardly from its contracted position, as shown typically in FIG. 3, to its extended position, as shown typically in FIG. 5. As described above, during the transition of the bellows 88 from the contracted position to the extended position, fluid is drawn through the fluid-flow aperture 86 in the lens support surface 78 and into the bellows to, in turn, create a vacuum or suction sufficient to transfer a contact lens CL from the eye onto the lens holder and remover 74. As shown typically in FIG. 5, in the extended position, the drive member 38 is withdrawn axially into the interior of the housing 14 with the removed contact lens CL seated on the lens support surface 78. The contact lens CL then may be either disposed of, or transferred to a lens storage container by employing a contact lens transfer device and/or associated method as disclosed in the above-mentioned co-pending patent application. As also shown typically in FIG. 5, in the extended position, the lobe 106 of the male housing 98 is releasably retained within a recess 108 of the female housing 96 to prevent further axial outward movement of the male housing relative to the female housing. During application of a contact lens CL onto an eye, and as shown typically in FIG. 1, the bellows 88 is maintained in the extended position to allow the drive member 38 and lens holder and remover 74 to be moved axially outwardly to apply the contact lens CL to the eye without creating suction within the lens support surface 78. To remove a contact lens from an eye, on the other hand, the male bellows housing 98 is manually pressed inwardly until the lobe 106 is releasably retained within the actuation aperture 100 to thereby load the bellows and ready the apparatus for contact lens removal. The male bellows housing 98 includes a peripheral base 4-08- 110 on the outer end thereof to allow the apparatus to stand vertically thereon for storage and/or when applying a contact lens to an eye.

In the operation of the apparatus 10, and as shown typically in FIG. 1, in order to apply a contact lens CL to an eye, the contact lens CL is placed onto the lens support surface 78 of the lens holder and remover 74. Preferably, the contact lens CL is transferred from its blister pack or other storage container (not shown) onto the lens support surface 78 by employing a contact lens transfer device and/or associated method as disclosed in the above-mentioned co-pending patent application. If desired, the apparatus 10 may be oriented vertically with the base 110 seated on a table or other support surface and the wing-shaped members 34 facing upwardly and opened outwardly. The user then moves his or her eye intended to receive the contact lens CL over the wing-shaped members 34 so that the support surfaces 36 contact the facial tissue surrounding the eye. If desired, however, the user need not place the apparatus 10 on a support surface, but rather the user may hold the apparatus in one hand and move the apparatus onto the facial tissue surrounding the eye, or another person, such as a physician or ophthalmic technician, may hold the apparatus and apply the contact lens CL to the person's eye. The trigger 16 is then manually depressed which, in turn, moves the first-tissue engaging surface 30 of the roller 24 in a counterclockwise direction and simultaneously moves the second tissue-engaging surface 32 of the curved cantilever in a clockwise direction, to thereby engage and move the tissue adjacent to each of the respective eyelids outwardly and retain the eye open during application of the contact lens CL thereto. Actuation of the trigger 16 simultaneously moves the drive member 38 from its retracted position, shown typically in FIG. 2, into its extended position, shown typically in FIG. 1. In the extended position, and as shown typically in FIG. 1, the contract lens CL seated on the contact lens support surface 78 is gently moved into contact with the eye. If the user looks directly at the contact lens CL, the contact lens is automatically placed onto the exposed cornea of the eye. If, on the other hand, the user looks to one side, the contact lens CL is automatically placed onto the eye adjacent to the cornea, and thus onto a less sensitive region of the eye. Upon placing the contact lens CL on the eye, the drive member 38 may gently depress the bellows 80 of the lens holder and remover 74, which in turn may cause fluid within the bellows to flow outwardly and thereby facilitate release of the contact lens therefrom and onto the user's eye. As shown typically in FIG. 1, a spring 112 is seated between the trigger 16 and bellows housing 90. After the contact lens CL touches the eye, the user may move the apparatus away from the eye (or move his or her face away from the apparatus if it is seated, for example, on a table or other support surface) and release the trigger 16. This, in turn, allows that spring 112 to drive the trigger 16 laterally outwardly into its normal position, and to axially withdraw the lens holder and remover 74 and pusher 38 to the normal position shown in FIG. 2.

Figure 3:
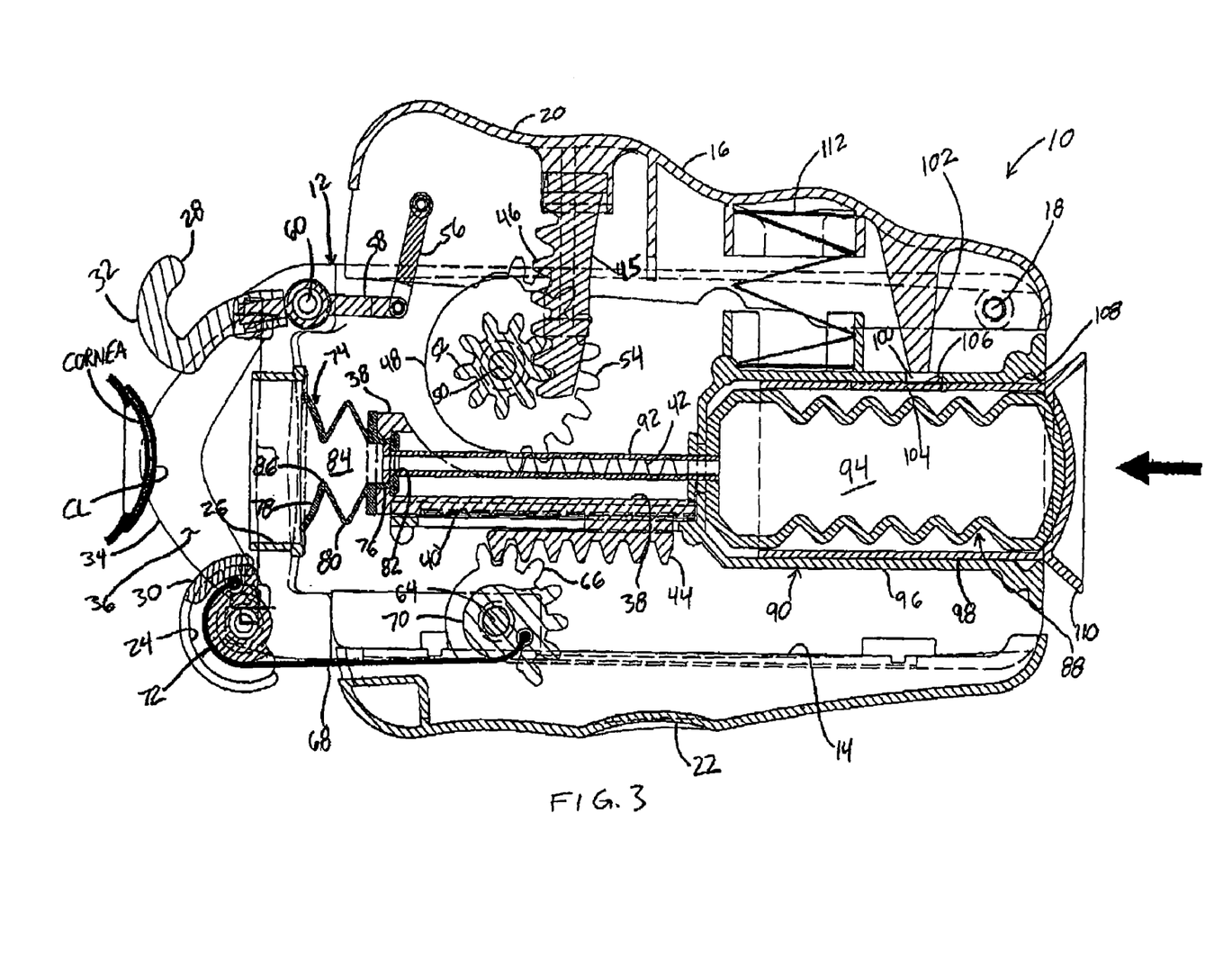
FIG. 3 is a cross-sectional view of the apparatus of FIG. 1 illustrating the bellows in a manually loaded state ready for removing a contact lens from an eye.

In order to remove the contact lens CL from the eye, and as shown typically in FIG. 3, the male bellows housing 98 is manually pushed laterally inwardly to load the bellows. As shown in FIG. 4, the user then moves his or her eye from which the contact lens CL is to be removed over the wing-shaped members 34 so that the support surfaces 36 contact the facial tissue surrounding the eye. If desired, however, the user need not place the apparatus on a support surface, but rather may simply hold the apparatus in one hand and move the apparatus onto the facial tissue surrounding the eye. The trigger 16 is then manually depressed which, in turn, moves the first-tissue engaging surface 30 of the roller 24 in a counterclockwise direction and simultaneously moves the second tissue-engaging surface 32 of the curved cantilever 28 in a clockwise direction to thereby engage and move the tissue adjacent to each of the respective eyelids outwardly and retain the eye open during removal of the contact lens CL from the eye. Actuation of the trigger 16 simultaneously moves the drive member 38 from its retracted position, shown typically in FIG. 3, into its extended position, shown typically in FIGS. 4 and 5. In the extended position, and as shown typically in FIG. 4, the contact lens support surface is moved gently into contact with the contact lens CL seated on the user's eye. When the trigger 16 is pivoted laterally inwardly, the second actuating arm 102 of the trigger engages and depresses laterally inwardly the lobe 106 of the tang 104 to thereby release the male housing 98 from the female housing 96. Then, the spring force of the contracted bellows 88 drives the bellows axially outwardly from its contracted position, as shown typically in FIG. 3, to its extended position, as shown typically in FIG. 5. As described above, during the transition of the bellows 88 from the contracted position to the extended position, fluid is drawn through the fluid-flow aperture 86 in the lens support surface 78 and into the variable-volume chamber 94 of the bellows 88 to, in turn, transfer the contact lens CL from the eye onto the lens holder and remover. As shown typically in FIG. 5, in the extended position, the drive member 38 is withdrawn axially into the interior of the housing 14 with the removed contact lens CL seated on the lens support surface 78. The contact lens CL then may be either disposed of, or transferred to a lens storage container by employing a contact lens transfer device and/or associated method as disclosed in the above-mentioned co-pending patent application. The bellows 88 is preferably made of a polymeric material, and is constructed such that it creates a sufficient spring force when located in the contracted position to drive itself into the extended position and create a sufficient vacuum or suction through the fluid-flow aperture 86 to effect a transfer of the contact lens CL from the eye and onto the lens support surface 78 of the lens holder and remover 74.

As may be recognized by those of ordinary skill in the pertinent art based on the teachings herein, numerous changes and modifications may be made to the above-described and other embodiments of the present invention with departing from the scope of the invention as defined in the appended claims. For example, the mechanism for effecting transfer of the lens onto the lens holder and remover may take any of numerous different configurations that are currently known, or that later become known for performing this function. As one example, a suction or vacuum may be created by employing a mechanism other than a bellows, such as a pump. Similarly, the other components of the apparatus may take any of numerous different shapes and/or configurations that are currently known, or that later become known for performing the function of the respective component. For example, the tissue-engaging surfaces may be formed of any of numerous different structures or devices. The actuator or trigger likewise may take any of numerous shapes or configurations that are currently known, or that later become known for performing this function, and the apparatus may include more than one actuator or trigger. In addition, the components of the apparatus may be made of any of numerous different materials that are currently known, or that later become known. Still further, the apparatus may be configured only for contact lens removal, rather than both contact lens application and removal as described herein. Accordingly, this detailed description of a currently preferred embodiment is to be taken in an illustrative, as opposed to a limiting sense.

What is claimed is:

1. An apparatus comprising:
   first means for supporting the apparatus against facial tissue adjacent to an eye;
   second means for movably engaging the facial tissue adjacent to the eye and retaining the eye open during removal of a contact lens therefrom;
   third means for removing the contact lens from the eye; and
   fourth means for actuating the second and third means to thereby facilitate retaining the eye open and to remove the contact lens therefrom.

2. An apparatus as defined in claim 1, wherein the fourth means is at least one actuating member.

3. An apparatus as defined in claim 1, wherein the second means is at least one tissue-engaging surface.

4. An apparatus as defined in claim 3, wherein the at least one tissue-engaging surface is defined by at least one of a curved cantilever and a roller.

5. An apparatus as defined in claim 1, wherein the first means is a support surface.

6. An apparatus as defined in claim 5, wherein the support surface is defined by at least two arcuate surfaces extending outwardly of an open proximal end of the apparatus to form an eyecup for locating the apparatus against an eye.

7. An apparatus as defined in claim 1, wherein the third means is a lens removing member.

8. An apparatus as defined in claim 1, wherein the third means includes means for holding a contact lens.

9. An apparatus as defined in claim 1, wherein the third means is adapted to hold a contact lens and is movable between a retracted and an extended position for applying the contact lens to the eye.

10. An apparatus as defined in claim 9, wherein the fourth means actuates the second and third means to thereby retain the eye open during application of the contact lens thereto.

11. An apparatus comprising:
    first means for supporting the apparatus against facial tissue adjacent to an eye;
    second means for movably engaging the facial tissue adjacent to the eye and retaining the eye open during removal of a contact lens therefrom;

third means for removing the contact lens from the eye, the third means including a contact lens support surface, at least one fluid-flow aperture extending through the lens support surface, and a suction chamber coupled in fluid communication with the at least one fluid-flow aperture for drawing fluid through the at least one fluid-flow aperture and, in turn, moving the lens from the eye and onto the lens support surface; and fourth means for actuating the second means and third means to thereby facilitate retaining the eye open and to remove the contact lens therefrom.

12. An apparatus as defined in claim 11, wherein the suction chamber is a variable-volume chamber movable between contracted and expanded positions for drawing fluid through the at least one fluid-flow aperture and into the chamber.

13. An apparatus as defined in claim 12, wherein the variable-volume chamber is defined by a bellows.

14. An apparatus as defined in claim 12, wherein the variable-volume chamber is adapted to move from the contracted to the expanded position in connection with the fourth means actuating the second and third means.

15. An apparatus comprising:
at least one actuator;
at least one tissue-engaging surface drivingly coupled to the actuator for engaging tissue adjacent to the eye in connection with actuating the actuator and facilitate retaining the eye open;
a support surface for supporting the apparatus adjacent to the eye;
a lens removing member drivingly coupled to the at least one actuator for movement between an extended position and a retracted position for removing the contact lens from the eye, wherein the at least one actuator actuates the at least one tissue-engaging surface to facilitate retaining the eye open during removal of the contact lens therefrom and actuates the lens removing member to remove the contact lens from the open eye.

16. An apparatus as defined in claim 15, wherein the at least one tissue-engaging surface is selected from a roller rotatably mounted on the apparatus, and a curved member pivotally mounted on the apparatus.

17. An apparatus as defined in claim 15, further comprising at least one biasing member coupled to the lens removing member for biasing the lens moving member toward the retracted position.

18. An apparatus as defined in claim 15, further comprising at least one rack and pinion coupled between the at least one actuator and the at least one tissue-engaging surface, wherein the rack meshes with the pinion to move the at least one tissue-engaging surface in connection with actuating the at least one actuator.

19. An apparatus as defined in claim 15, wherein the at least one actuator is pivotally mounted on the apparatus and includes an actuating surface, and the lens removing member includes a cam surface engageable with the actuating surface upon pivoting the actuator to thereby move the lens removing member between the extended and retracted positions.

20. An apparatus as defined in claim 15, wherein the support surface is defined by at least one support member pivotally mounted on the housing.

21. An apparatus as defined in claim 20, wherein the support surface conformably contacts facial tissue adjacent to the eye.

22. An apparatus as defined in claim 15, wherein the lens removing member includes lens support surface and a flexible portion coupled to the lens support surface.

23. An apparatus as defined in claim 15, wherein the lens removing member is adapted to hold a contact lens and is movable between a retracted and an extended position for applying the contact lens to the eye.

24. A method for removing a contact lens from an eye, comprising the following steps:
providing an apparatus including a lens removing member movably mounted thereon, at least one actuator for moving the lens removing member between an extended position and retracted position, and at least one tissue-engaging surface drivingly coupled to the at least one actuator and movably mounted on the apparatus;
placing the apparatus adjacent to the eye with the at least one tissue-engaging surface in contact with facial tissue adjacent to the eye; and
actuating the at least one actuator to move the at least one tissue-engaging surface against facial tissue adjacent to the eye and facilitate retaining the eye open, move the lens removing member from the retracted to the extended position and, in turn, transfer the lens from the eye onto the lens removing member.

25. A method as defined in claim 24, further comprising the step of drawing fluid through the lens removing member to in turn draw the lens from the eye and onto the lens removing member.

26. A method as defined in claim 25, wherein the fluid is drawn through the lens removing member in connection with moving the lens removing member from the retracted position to the extended position.

27. An apparatus comprising:
at least one actuator;
at least one tissue-engaging surface drivingly coupled to the actuator for engaging tissue adjacent to the eye in connection with actuating the actuator and facilitate retaining the eye open;
a support surface for supporting the apparatus adjacent to the eye;
a lens removing member drivingly coupled to the at least one actuator for movement between an extended position and a retracted position for removing the contact lens from the eye, wherein the at least one actuator actuates the at least one tissue-engaging surface to facilitate retaining the eye open during removal of the contact lens therefrom and actuates the lens removing member to remove the contact lens from the open eye; and
at least one biasing member coupled to the lens removing member for biasing the lens removing member toward the retracted position, wherein at least one of the at least one biasing member is a bellows.

* * * * *